United States Patent
Teoh et al.

(10) Patent No.: US 6,566,435 B1
(45) Date of Patent: May 20, 2003

(54) ELASTOMERIC GLOVES

(75) Inventors: Seng Chin Teoh, Penang (MY); Seong Fong Chen, Penang (MY)

(73) Assignee: LRC Products Limited, Hertfordshire (GB)

( * ) Notice: Subject to any disclaimer, the term of this patent is extended or adjusted under 35 U.S.C. 154(b) by 0 days.

(21) Appl. No.: 09/807,535

(22) PCT Filed: Oct. 13, 1999

(86) PCT No.: PCT/GB99/03470

§ 371 (c)(1),
(2), (4) Date: Apr. 13, 2001

(87) PCT Pub. No.: WO00/21451

PCT Pub. Date: Apr. 20, 2000

(30) Foreign Application Priority Data

Oct. 13, 1998 (GB) ............................................. 9822358

(51) Int. Cl.⁷ ............................................. C08L 13/02
(52) U.S. Cl. ........................ 524/432; 524/430; 524/478; 524/560; 524/562; 525/478; 2/168; 128/844
(58) Field of Search ................................. 524/560, 562, 524/432, 430, 478; 525/478; 2/168; 128/844

(56) References Cited

U.S. PATENT DOCUMENTS

| | | | |
|---|---|---|---|
| 2,880,189 A | | 3/1959 | Miller et al. ................. 524/821 |
| 5,284,157 A | * | 2/1994 | Miller et al. ................. 128/844 |
| 5,369,166 A | * | 11/1994 | Ozawa et al. ................ 524/560 |
| RE35,616 E | * | 9/1997 | Tillotson et al. ................ 2/167 |
| 5,749,202 A | * | 5/1998 | Eichbauer ..................... 53/399 |
| 5,872,173 A | * | 2/1999 | Anand ......................... 524/494 |
| 5,886,111 A | * | 3/1999 | Chiotis et al. ............... 525/106 |
| 6,020,070 A | * | 2/2000 | Hoerner et al. ........... 428/423.1 |
| 6,329,444 B1 | * | 12/2001 | McGlothlin et al. ......... 523/105 |
| 6,369,154 B1 | * | 4/2002 | Suddaby ...................... 524/560 |

FOREIGN PATENT DOCUMENTS

| | | |
|---|---|---|
| DE | 9618006 | 11/1997 |
| EP | 0456333 | 11/1991 |
| EP | 0559150 | 9/1993 |
| WO | 9748765 | 12/1997 |
| WO | 9906481 | 2/1999 |

* cited by examiner

Primary Examiner—David W. Wu
Assistant Examiner—Henry S. Hu
(74) Attorney, Agent, or Firm—Stevens, Davis, Miller & Mosher, L.L.P.

(57) ABSTRACT

An elastomeric carboxylated nitirle rubber glove has a stress retention, after six minutes at 100% extension, of rom 50% to 70%. It is made using prevulcanized carboxylated nitrile rubber latex with 2 to 6% by weight methacrylic acid equivalent.

14 Claims, No Drawings

ELASTOMERIC GLOVES

This invention relates to elastomeric gloves, particularly but not exclusively medical and surgical gloves, and to a method of making them.

Close fitting rubber gloves are well known and are used for a number of purposes, principally medical and surgical. It is especially important in some uses for the gloves to fit closely on the hand, at least in the finger and palm regions. To ensure this close fitting, it is customary for users to wear gloves of slightly smaller dimensions than their hands in order to ensure a close snug fit. However, some discomfort can arise during use of the gloves, from the continued application of pressure by the glove on the hand.

It has been proposed in EP-B-0456333 to overcome this problem by making such gloves of nitrile butadiene rubber since this material has long been known to show stress relaxation properties. In particular, the patent describes gloves made of a carboxylated elastomeric material comprising 0.1 to 0.5 parts zinc oxide per 100 parts carboxylated nitrile butadiene rubber, the material being such that when stretched 100% of its length with an initial stress and the 100% stretch maintained, the material relaxes within 6 minutes of the initial stress so that the 100% stretch is maintained by a reduced stress which is less than 80%, more preferably less than 50%, of the initial stress. The effect of this is that whilst the gloves are tight fitting when initially donned, the stress subsequently relaxes within six minutes so as to relieve the pressure applied to the user's hands and so provide greater comfort and sensitivity. In the only Example in the patent, the stress retention of a carboxylated nitrile butadiene rubber glove was 0% after six minutes.

Whilst this basic approach of using the known stress relaxation properties of carboxylated nitrile rubbers does provide some alleviation of the problem of user discomfort due to stress retention in rubber gloves, it does not provide a wholly satisfactory answer. In particular, we have found that the stress retention which occurs in known carboxylated nitrile rubbers such as taught by EP-B-0456333 is actually too low such that its use can result in poor fitting of gloves to the hands and fingers as the gloves gradually become loose with time because of creep due to stress relaxation. In particular, we have found that stress retention of less than 50% as is found in known such rubbers, can give rise to problems and that, surprisingly, far improved user comfort and satisfaction is achieved with a stress retention of from about 50 to about 70%.

Copolymer latices containing carboxyl-modified nitrile rubber and a diene are disclosed in EP 0559150A. Such latices can be used to provide rubber articles having high oil resistance and high mechanical strength.

Accordingly, in one aspect, the present invention provides an elastomeric glove made of a carboxylated nitrile rubber having from 2 to 6% by weight methacrylic acid equivalent and which exhibits a stress retention of from 50 to 70%, said stress retention being the percentage retention of the initial stress after six minutes at 100% extension. Gloves of the invention give better fitting to the hands and fingers and hence improved sensitivity of touch on extended wearing compared with those that have low stress retention of less than 50%.

The stress retention of the gloves produced according to the present invention is higher than that illustrated and obtained by EP-B-0456333, but lower than that of gloves made from natural rubber latex or polychloroprene latex. The gloves of the invention can be made to be good fitting and yet not to cause fatigue to the hands on extended wearing.

Gloves made of conventional carboxylated nitrile rubbers have a low stress retention, i.e. well below 50%. Accordingly, gloves of the present invention cannot be made by simply using known nitrile rubber glove technology since the stress retention would then be too low. We have found, however, that stress retention can be controllably increased to the levels required in the present invention by using prevulcanised nitrile butadiene rubber latex, i.e. latex in which some vulcanisation of the rubber by sulphur has been effected before the gloves are made. Prevulcanisation (or maturation) of the rubber in this way then enables the desired stress retention of 50 to 70% to be obtained following a conventional dipping production process.

The gloves of the invention can be non-chlorinated or chlorinated or polymer-coated, as desired. The carboxylated nitrile rubber latex used to make the gloves is preferably a copolymer of acrylonitrile, butadiene, and an unsaturated carboxylic acid. The unsaturated carboxylic acid is of acrylic acid type and may be, for example, acrylic acid, methacrylic acid, crotonic acid, itaconic acid, fumaric acid, or sorbic acid. Methacrylic acid is preferred. The ratio of acrylonitrile to butadiene in the copolymer will depend upon the use to which the glove is to be put. For an industrial glove requiring good resistance to organic solvents, the acrylonitrile content may be as high as 37 to 40% of the polymer. For surgical and other medical gloves, solvent resistance is much less important than softness and flexibility. In this case, a copolymer of much lower acrylonitrile content is used, usually about 26 to 30% of the polymer. The preferred amount of unsaturated carboxylic acid is 2–6% methacrylic acid equivalent, most preferably 3–5.5% methacrylic acid equivalent.

In the gloves of the invention, the nitrile rubber is cross-linked both by conventional vulcanisation (i.e. by sulphur, vulcanisation accelerators and zinc oxide), and by ionic crosslinking using polyvalent metal oxides, preferably zinc oxide. The amount of polyvalent metal oxide (eg. zinc oxide) used for the ionic cross-linking is preferably from about 0.1 to 0.5 phr (per hundred parts of nitrile rubber, dry basis), more preferably from 0.2 to 0.4 phr. The polyvalent metal oxides effect crosslinking ionically between carboxylate groups in the polymer chain. The amount of sulphur used for crosslinking is from 1 to 3 phr, preferably from 2 to 3 phr. The crosslinking of the nitrile polymers achieved by sulphur crosslinks (both during the process and during prevulcanisation) is the major effect and the ionic crosslinking via the polyvalent metal oxide and the carboxyl groups is the minor effect. The selection of a low level of carboxylation and of a low polyvalent metal oxide level keep the level of ionic crosslinks in the nitrile rubber relatively low. Ionic crosslinks exhibit higher stress relaxation characteristics than do sulphur crosslinks. The stress retention achieved can be controlled by varying the amounts of, and balance between, the two types of crosslink.

According to the invention, the carboxylated nitrile rubber latex is subjected to a prevulcanisation (or maturation) step. Preferably, this is at least at 30° C. for a minimum of 16 hours for fully compounded latex. As will be clear to those skilled in the art, however, different temperatures and times can be used to provide essentially the same effect and the invention encompasses these equivalents. In general, lower temperatures will require longer times, and higher temperatures shorter times. The practical minima and maxima will be readily determinable by those skilled in the art with any particular latex formulation, bearing in mind the ultimate purpose of providing gloves with a stress retention of from 50 to 70%.

In order that the invention may be more fully understood, the following Examples are given by way of illustration only.

Carboxylated acrylonitrile butadiene latices with a carboxylation level of 4%–6% methacrylic acid equivalent content were compounded according to Formulation A given in Table 1. Formulation B given in Table 2 has also been used. The latex was prevulcanized for 40° C. for various periods of time. Prevulcanization at 50° C. of has also been used. After the required heating time, the latex was cooled. Gloves were prepared from the prevulcanized latex by well-know procedures, involving the steps of coagulant dipping, leaching, drying and vulanizing. The gloves were then finished, either by washing and powdering, or by washing and chlorination, as indicated in the Examples that follow.

The gloves were tested according to ASTM methods.

In the following Examples, carboxylated acrylonitrile butadiene rubber is referred to as XNBR, zinc dibutyl dithiocarbamate as ZBuD, zinc mercaptobenzthiazole as ZMBT and zinc diethyl dithiocarbamate as ZDEC.

Examples 1–3 illustrate that conventional nitrile rubber formulations containing zinc oxide levels above 1 phr produce gloves with stress retention less than 50%.

EXAMPLE 1

Carboxylation level of nitrile polymer in latex=ca. 6% methacrylic acid

| Formulation | phr |
| --- | --- |
| XNBR | 100 |
| S | 2.0 |
| ZBuD | 1.0 |
| ZMBT | 0.5 |
| ZnO | 2.0 |

Latex maturation at ambient temperature, 30° C.±4° C. for 24 hours. Stress retention of gloves produced=45%

EXAMPLE 2

Carboxylation level of nitrile polymer in latex=ca. 6% methacrylic acid

| Formulation | phr |
| --- | --- |
| XNBR | 100 |
| S | 1.0 |
| ZBuD | 0.25 |
| ZnO | 2.8 |

Latex maturation at ambient temperature, 30° C.±4° C. for 6 days. Stress retention of gloves produced=38%

EXAMPLE 3

Carboxylation level of nitrile polymer latex=ca. 4% methacrylic acid

| Formulation | phr |
| --- | --- |
| XNBR | 100 |
| ZDEC | 0.5 |
| ZMBT | 0.5 |
| ZnO | 4.0 |
| S | 1.0 |

Latex maturation at ambient temperature, 30° C.±4° C. for 4 days. Stress retention of gloves produced=42%

EXAMPLE 4

This Example illustrates that ionic crosslinks using a formulation containing zinc oxide only (no sulphur vulcanisation occurs) produces gloves with low stress retention of about 30%.

Carboxylation level of nitrile polymer in latex=ca. 4% methacrylic acid

| Formulation | phr |
| --- | --- |
| XNBR | 100 |
| ZnO | 1.5 |

Latex prevulcanisation at 40° C. for 48 hours, 72 hours, 96 hours and 168 hours.

Stress retention of gloves produced in all cases=30±2%

Examples 5–8 illustrate the use of Formulation A to produce gloves with stress retention>50%. Physical properties of the gloves are also given.

In the following examples, the meanings of M500 and EB are:

M500=the stress (in MPa) at 500% strain

EB%=elongation percentage at break.

EXAMPLE 5

Carboxylation level of nitrile polymer in latex=ca. 4% methacrylic acid

| Formulation | phr |
| --- | --- |
| XNBR | 100 |
| S | 2.0 |
| ZDEC | 0.75 |
| ZnO | 0.25 |

Latex prevulcanisation at 40° C. for 48 hours–96 hours.

| Time, | Stress retention % | | Tensile strength, MPa | | M500 MPa | | EB, % | |
| --- | --- | --- | --- | --- | --- | --- | --- | --- |
| hr | ncl | cl | ncl | cl | ncl | cl | ncl | cl |
| 48 | 62 ± 2 | 62 ± 2 | 17.7 | 16.6 | 5.5 | 5.3 | 660 | 660 |
| 72 | 66 ± 2 | 63 ± 3 | 18.5 | 15.0 | 6.0 | 5.7 | 640 | 630 |
| 96 | 63 ± 3 | 61 ± 3 | 19.4 | 17.4 | 7.5 | 6.6 | 615 | 635 | ncl—non-chlorinated gloves
cl—chlorinated gloves

EXAMPLE 6

This Example illustrates that by reducing the ZDEC level in Example 5, gloves with lower modulus, M500, are produced.

Carboxylation level of nitrile polymer in latex=ca. 4% methacrylic acid

| Formulation | phr |
|---|---|
| XNBR | 100 |
| S | 2.0 |
| ZDEC | 0.50 |
| ZnO | 0.25 |

Latex prevulcanisation at 40° C. for 48 hours–96 hours

| Time, hr | Stress retention % ncl | Stress retention % cl | Tensile strength, MPa ncl | Tensile strength, MPa cl | M500, MPa ncl | M500, MPa cl | EB, % ncl | EB, % cl |
|---|---|---|---|---|---|---|---|---|
| 48 | 56 ± 2 | 54 ± 3 | 16.1 | 17.7 | 4.3 | 4.1 | 710 | 735 |
| 72 | 62 ± 4 | 57 ± 2 | 15.9 | 16.1 | 4.1 | 4.1 | 715 | 725 |
| 96 | 60 ± 2 | 56 ± 2 | 16.0 | 19.8 | 4.1 | 4.9 | 720 | 725 |

EXAMPLE 7

Carboxylation level of nitrile polymer in latex=ca. 5.5% methacrylic acid

| Formulation | phr |
|---|---|
| XNBR | 100 |
| S | 2.0 |
| ZDEC | 0.75 |
| ZnO | 0.30 |

Latex prevulcanisation at 40° C. for 48, 72, 96 and 168 hours.

| Time, hr | Stress retention % ncl | Stress retention % cl | Tensile strength, MPa ncl | Tensile strength, MPa cl | M500, MPa ncl | M500, MPa cl | EB, % ncl | EB, % cl |
|---|---|---|---|---|---|---|---|---|
| 48 | 55 ± 1 | 55 ± 2 | 21.4 | 26.8 | 4.6 | 5.9 | 690 | 685 |
| 72 | — | — | 25.8 | 28.3 | 4.9 | 5.9 | 690 | 685 |
| 96 | 59 ± 3 | 59 ± 1 | 28.8 | 26.6 | 6.4 | 5.4 | 660 | 690 |
| 168 | 65 ± 2 | 59 ± 2 | 25.0 | 23.9 | 5.7 | 4.8 | 670 | 690 |

EXAMPLE 8

This Example illustrates that when the carboxylation level of the nitrile latex is high at 6% methacrylic acid content, the stress retention of the gloves produced is reduced compared with Examples 5–7.

Carboxylation level of nitrile polymer in latex=ca. 6% methacrylic acid

| Formulation | phr |
|---|---|
| XNBR | 100 |
| S | 2.0 |
| ZDEC | 0.75 |
| ZnO | 0.30 |

Latex prevulcanisation at 40° C. for 48 hours–168 hours

| Time, hr | Stress retention % ncl | Stress retention % cl | Tensile strength, MPa ncl | Tensile strength, MPa cl | M500, MPa ncl | M500, MPa cl | EB, % ncl | EB, % cl |
|---|---|---|---|---|---|---|---|---|
| 48 | 53 ± 1 | 49 ± 3 | 37.7 | 49.0 | 11.8 | 24.7 | 610 | 560 |
| 72 | 50 ± 1 | 52 ± 2 | 36.8 | 37.2 | 7.8 | 9.0 | 680 | 670 |
| 168 | 52 ± 3 | 51 ± 1 | 21.6 | 19.0 | 2.2 | 2.7 | 715 | 695 |

EXAMPLE 9

This Example illustrates the use of Formulation B to produce gloves with stress retention>50%.

Carboxylation level of nitrile polymer in latex=ca. 4% methacrylic acid

| Formulation | phr |
|---|---|
| XNBR | 100 |
| S | 2.0 |
| ZDEC | 0.35 |
| ZMBT | 0.35 |
| DPG | 0.65 |
| ZnO | 0.20 |

Latex prevulcanisation at 40° C. for 48, 72 hours and 96 hours

| Time, hr | Stress retention % ncl | Stress retention % cl | Tensile strength, MPa ncl | Tensile strength, MPa cl | M500, MPa ncl | M500, MPa cl | EB, % ncl | EB, % cl |
|---|---|---|---|---|---|---|---|---|
| 48 | 57 ± 1 | 58 ± 1 | 20.4 | 20.3 | 7.9 | 8.0 | 610 | 615 |
| 72 | 59 ± 1 | 56 ± 1 | 18.9 | 19.6 | 6.1 | 5.7 | 650 | 660 |
| 96 | 62 ± 3 | 57 ± 3 | 19.7 | 22.4 | 6.5 | 6.6 | 650 | 655 |

The difference between formulation A and formulation B is in the accelerators used. A general formulation is shown in Table 3.

TABLE 1

Nitrile Latex Formulation A

| | phr |
|---|---|
| XNBR | 100.0 |
| Potassium hydroxide | 0–0.5 |
| Sodium dodecyl benzene sulphonate | 0.1–0.5 |
| Ammonia solution | to adjust pH to ca. 9.5 |
| Sulphur | 1–3 |
| Zinc diethyl dithiocarbamate | 0.2–1.0 |
| Zinc oxide | 0.1–0.5 |
| Wingstay L | 0–1.0 |
| Titanium dioxide | 2.0–5.0 |

TABLE 1-continued

Nitrile Latex Formulation A

| | phr |
|---|---|
| Coagulant WS | 0–2.0 |
| Water | to dilute latex to 30%–35% total solids content |
| Pigment | 0–0.5 |

TABLE 2

Nitrile Latex Formulation B

| | phr |
|---|---|
| XNBR | 100.0 |
| Potassium hydroxide | 0–0.5 |
| Sodium dodecyl benzene sulphonate | 0.1–0.5 |
| Ammonia solution | to adjust pH to ca. 9.5 |
| Sulphur | 1–3 |
| Zinc diethyl dithiocarbamate | 0.20–1.0 |
| Zinc mercaptobenzthiazole | 0.2–0.5 |
| Diphenyl guanidine | 0.4–0.8 |
| Zinc oxide | 0.1–0.5 |
| Wingstay L | 0–1.0 |
| Titanium dioxide | 2.0–5.0 |
| Coagulant WS | 0–2.0 |
| Water | to dilute latex to 30%–35% total solids content |
| Pigment | 0–0.5 |

TABLE 3

General Nitrile Formulation

| | phr |
|---|---|
| XNBR | 100.0 |
| Potassium hydroxide | 0–0.5 |
| Sodium dodecyl benzene sulphonate | 0.1–0.5 |
| Ammonia solution | to adjust pH to ca. 9.5 |
| Sulphur | 1–3 |
| Vulcanisation accelerator(s) | 0.2–2.5 |
| Zinc oxide | 0.1–0.5 |
| Wingstay L | 0–1.0 |
| Titanium dioxide | 2.0–5.0 |
| Coagulant WS | 0–2.0 |
| Water | to dilute latex to 30%–35% total solids content |
| Pigment | 0–0.5 |

What is claimed is:

1. An elastomeric glove made of a carboxylated nitrile rubber having from 2 to 6 % by weight methacrylic acid equivalent and which exhibits a stress retention of from 50% to 70%, said stress retention being the percentage retention of the initial stress after six minutes at 100% extension, when wherein prevulcanized rubber latex is used to form the glove.

2. A glove according to claim 1, which contains from 3 to 5.5% by weight methacrylic acid equivalent.

3. A glove according to claim 1, in which the carboxylated nitrile rubber has been cross-linked with from 1 to 3 phr sulphur and less than 0.5 phr polyvalent metal oxide.

4. A glove according to claim 3, wherein from 0.5–1.5 phr vulcanisation accelerator is used.

5. A glove according to claim 3, wherein the polyvalent metal oxide is zinc oxide.

6. A glove according to claim 1, wherein the carboxylated nitrile rubber is a copolymer of acrylonitrile, butadiene and an unsaturated carboxylic acid.

7. A glove according to claim 6, wherein the unsaturated carboxylic acid is of acrylic acid type.

8. A glove according to claim 7, wherein the carboxylic acid is acrylic acid, methacrylic acid, crotonic acid, itaconic acid, fumaric acid or sorbic acid.

9. A glove according to claim 1, which contains up to 40% nitrile content and is an industrial solvent-resistant glove.

10. A glove according to claim 1, which contains up to 30% nitrile content and is a surgical or medical glove.

11. A glove according to claim 1, which exhibits a stress retention of from 55 to 70%.

12. A method of making a carboxylated nitrile rubber glove having a stress retention of from about 50% to about 70%, said stress retention being the percentage retention of the initial stress after six minutes at 100% extension, which method comprises dipping a former into a pre-vulcanised carboxylated nitrile rubber latex formulation, the rubber having from 2 to 6% methacrylic acid equivalent, the latex formulation containing from 1 to 3 phr sulphur, from 0.5 to 1.5 phr vulcanisation accelerator, and less than 0.5 phr polyvalent metal oxide.

13. A method according to claim 12, wherein the rubber latex has been prevulcanized by storage of the formulation at at least 30 ° C. for at least 16 hours, or the equivalent.

14. A method according to claim 12, wherein the formulation contains from 2 to 3 phr sulphur and from 0.1 to less than 0.5 phr zinc oxide.

* * * * *